United States Patent [19]

Becker et al.

[11] Patent Number: 4,480,127

[45] Date of Patent: Oct. 30, 1984

[54] PROCESS FOR THE PRODUCTION OF VARIABLE AMOUNTS OF DPA AND ANILINE USING ONLY PHENOL AND AMMONIA AS THE FEEDSTOCK

[75] Inventors: Mitchell Becker, Teaneck, N.J.; Howard M. Sachs, Riverdale, N.Y.

[73] Assignee: The Halcon SD Group, Inc., New York, N.Y.

[21] Appl. No.: 496,371

[22] Filed: May 20, 1983

[51] Int. Cl.$^3$ .............................................. C07C 85/06
[52] U.S. Cl. ................................................... 564/402
[58] Field of Search ........................................ 564/402

[56] References Cited

U.S. PATENT DOCUMENTS

| | | | |
|---|---|---|---|
| 3,272,865 | 9/1966 | Barker | 564/402 |
| 3,682,782 | 8/1972 | Choo | 564/402 X |
| 3,860,650 | 1/1975 | Becker et al. | 564/402 |
| 4,326,080 | 4/1982 | Wedemeyer et al. | 564/402 |

FOREIGN PATENT DOCUMENTS 1541153  2/1979  United Kingdom ................ 564/402

*Primary Examiner*—Paul F. Shaver
*Attorney, Agent, or Firm*—William C. Long; R. T. Stewart; D. R. Zirker

[57] ABSTRACT

A process for the production of predetermined variable amounts of diphenylamine and aniline from a feedstock consisting essentially of phenol and ammonia is disclosed. The process involves catalytically reacting phenol and ammonia to produce aniline in situ and then reacting part of the aniline with other phenol and aniline to produce DPA, with the remaining aniline being removed from the reaction media as product.

10 Claims, No Drawings

PROCESS FOR THE PRODUCTION OF VARIABLE AMOUNTS OF DPA AND ANILINE USING ONLY PHENOL AND AMMONIA AS THE FEEDSTOCK

BACKGROUND OF THE INVENTION

1. Field of the Invention

This invention is related to the preparation of variable amounts of diphenylamine (DPA) and aniline, and more particularly, is related to the preparation of DPA, using only a phenol-ammonia feedstock, from the resulting reaction of aniline (prepared in situ) with phenol.

2. Description of Prior Art

DPA is a well known industrial chemical having a variety of usages, such as in the production of anti-oxidants for elastomers and in the manufacture of azo dyes, and can be prepared by a variety of methods. Generally, it has been prepared commercially by catalytically deammoniating or self-condensing aniline. British Pat. No. 752,859 discloses such a process in which aniline is reacted in the presence of activated alumina or titania. U.S. Pat. No. 3,071,619 discloses a liquid phase process involving the use of NH$_4$BF$_4$ as the catalyst.

Processes for the production of aniline type compounds through the liquid or the vapor phase amination of phenolic compounds with ammonia have also been reported in the literature. Generally, these reactions take place at elevated pressures and temperatures, in the presence of catalysts containing silica and alumina. One such aniline reaction process is disclosed in U.S. Pat. No. 3,272,365, wherein phenol and ammonia are combined over a silica-alumina catalyst at temperatures between 400°–480° C. U.S. Pat. No. 3,860,650 describes a process for the production of organic amines by the amination of phenolic type compounds, using a catalyst consisting essentially of an alumina gel containing less than 1.0 wt. % of alkali metal.

It has been proposed to produce DPA by catalytically reacting aniline with phenol, viz;

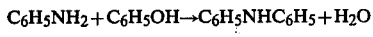

$$C_6H_5NH_2 + C_6H_5OH \rightarrow C_6H_5NHC_6H_5 + H_2O$$

Such a process is described in U.S. Pat. No. 2,824,137 employing a titanium catalyst; in British Pat. No. 1,541,153 using phosphoric acid as a catalyst, and in Japanese Patent Publication No. 75/07.061, which carries out the reaction in the presence of alumina. U.S. Pat. No. 3,944,613 discloses a liquid-phase process for the production of DPA which uses a silica/alumina catalyst. All of the processes described in these publications, however, are characterized by short catalyst lifetime, relatively high temperature operation, and subsequent catalyst separation problems. It has long been recognized that while phenolic type compounds frequently will easily react with aniline, the reaction of aniline with phenol itself is far more difficult to sustain.

U.S. application Ser. No. 431,532, filed Sept. 30, 1982, discloses a process for the production of variable amounts of aniline and DPA from an ammonia and phenol feedstock by using a two reactor process operation. This process essentially features the integration of an aniline plant with a DPA plant, and can achieve desired ratios of aniline/DPA by diverting at least a portion, if not all, of the formed aniline to the DPA plant. In contrast, the present invention can achieve any desired ratio of DPA to aniline using only a single reactor with the attendant savings in plant construction. Also, whereas the cited application discloses a preferred NH$_3$/phenol range of 10 to 25 molar, the present application takes cognizance of the effect the NH$_3$/phenol ratio has on DPA production and takes advantage of the fact that DPA production is increased at the lower NH$_3$ ratios.

Catalysts useful for the commercial production of organic amines such as DPA must satisfy certain performance characteristics if they are to prove satisfactory. Catalytic activity, often expressed in terms of the percentage of raw material conversion to the desired product under a particular process environment, is particularly a major concern. The more active a catalyst, the smaller the reaction space, or volume, required for a particular rate of production or, alternatively, the lower is the reaction temperature or flow rate which will be required for the desired production rate. Thus, it is of particular importance to utilize a catalyst which displays sufficient activity at relatively low temperatures, since the lower the operating temperature the greater is the desired selectivity of product, and the longer the catalyst life expectancy.

It is accordingly, an object of this invention to provide an improved process for the preparation of DPA using only a phenol and ammonia feedstock, from the catalytic reaction of aniline (prepared in situ) with phenol in a process having attractive conversions and high selectivities, and yet which avoids the drawbacks and disadvantages of prior art processes.

It is another object of this invention to produce variable amounts of DPA and aniline from a process using only phenol and ammonia as its feedstock, in an efficient and economical manner.

It is still another object of this invention to provide a catalyst useful for the production of both DPA and aniline which has high activity at relatively low reaction temperatures and which is particularly selective to the desired amination reaction.

SUMMARY OF THE INVENTION

It has now been determined that these and other objects of the invention have been achieved by a novel catalytic process for the production of predetermined, variable amounts of DPA and aniline, ranging from substantially all DPA to 1:99 wt. % of DPA/aniline, using a feedstock source consisting essentially of ammonia and phenol. The process, which can be either continuous or batch, contacts the makeup ammonia and phenol feed with a recycled phenol, ammonia and aniline stream; the range of operative compositions varying from about 100:1 to 1:20 molar of ammonia to phenol plus aniline (total organics present). The contacting can occur in either the liquid or vapor phase with a solid heterogeneous acidic catalyst, and most preferably a low alkali, acid treated, alumina gel. In the apparent reaction mechanism, phenol and ammonia rapidly react to form aniline in situ, which is circulated throughout the system, contacting and catalytically reacting with either phenol or, with another aniline present, to form DPA in two kinetically much slower reactions. By varying the relative ratios and amounts of phenol and ammonia feedstock, together with the amount of aniline, phenol and/or ammonia to be recycled, almost any conceivable end product ratio of DPA/aniline can be obtained from only an original phenol-ammonia feedstock and using but a single reactor system. DPA is separated, using standard techniques, from the reaction mixture, together with the desired amount of aniline product. The amount of phenol feed supplied and recycled is dependent upon the amount of DPA and aniline product desired; the ammonia feed reacts with phenol to replace the aniline consumed and the method surprisingly requires no external amount of aniline fed into the system.

DETAILED DESCRIPTION

The reaction for preparing DPA by the method of this invention is best represented by the following set of equations:

$$C_6H_5OH + NH_3 \rightarrow C_6H_5NH_2 + H_2O \tag{1}$$

$$C_6H_5NH_2 + C_6H_5OH \rightarrow C_6H_5NHC_6H_5 + H_2O \tag{2}$$

From an analysis of equations 1 and 2, it is quickly determined that the overall process reaction is as follows:

$$2C_6H_5OH + NH_3 \rightarrow C_6H_5NHC_6H_5 + 2H_2O; \tag{3}$$

e.g., DPA is produced from only an original phenol-ammonia feedstock. However, by using the process of this invention, both DPA and aniline can be produced in almost any product ratio desired. Using an effective solid heterogeneous acidic catalyst, e.g., a solid alumina gel catalyst, aniline is first produced in situ in the reaction zone by the mechanism described in equation (1), and the aniline product is then circulated within the reaction system contacting and eventually catalytically reacting with either a phenol molecule, or, a second aniline molecule; each reaction yielding DPA as a product. Both of these reactions are much slower kinetically than the formation of aniline from phenol and ammonia, and as such are the rate determining steps in the process. A sufficient amount of phenol must be introduced to form the desired amounts of both aniline and DPA, while enough ammonia must be introduced to replace the aniline consumed in the making of DPA and/or taken off as the desired product.

Although the reaction between phenol and ammonia to produce aniline and that between aniline and phenol to produce DPA both stoichiometrically require a one to one mole ratio of reactants, by varying the molar ratios of ammonia to phenol plus aniline (total organics) present in the reactor feed stream over a 100:1 to 1:20 range, together with the appropriate adjustments in the recycle ratio, the relative amounts of DPA and aniline produced can range from substantially all DPA to 1:99 wt. % DPA/aniline. For example, if DPA is the major product desired, the amount of ammonia feedstock should be reduced, relative to the phenol feedstock, and the amount of aniline recycled should be increased. If, however, aniline is the principal product desired, the ammonia feed should be increased, and the aniline recycle reduced. Also, if catalyst life is a primary consideration, the amount of ammonia present in the system can be either increased (increasing catalyst life), or, reduced if catalyst life is not considered a significant parameter. Thus, the surprising end result of the process is that predetermined and greatly variable amounts of DPA and aniline can be produced from a single catalytic process and a unitary reactor system, using only a cheap and widely available phenol and ammonia feedstock, in an efficient and economical manner.

Although the reactions involved in the process may be carried out in a system primarily maintained in the vapor phase, wherein the chemicals are first prevaporized and then passed through a catalyst bed maintained under appropriate pressure and temperature conditions, it is preferred that the reaction be carried out in a substantially one phase, liquid phase system, wherein liquid phenol and liquid ammonia are initially brought into contact with the solid, heterogeneous acidic catalyst.

Liquid phase reaction is preferred since, although it is not wished to be bound by theory, operating in a one phase, liquid phase system apparently greatly extends catalyst life by keeping a substantial amount of the water in the liquid phase, in which water does not seem to be able to damage the catalyst as severely as when it exists in the vapor phase. The liquid phase embodiment is, of course, carried out under the appropriate pressure conditions. However, due to economic consideration and the magnitude of the pressures required for certain liquid phase operation, particularly when dealing with a substantial excess of ammonia at temperatures above which it is readily condensable, some vapor phase operation will be required.

The above reactions in this process can be conducted at temperatures ranging from about 200° to 500° C.; and, preferably, from 300° to 420° C. At temperatures below 300° C., the reaction proceeds too slowly, whereas at temperatures in excess of 420° C. the selectivity of the reaction to the desired products decreases, and the reaction system further requires extremely high pressures to maintain aniline in the liquid phase. Temperature is known to cause a substantial effect on reaction selectivity, and in this process to form DPA it is essential from a commercial standpoint to operate below 420° C.

As stated above, when the reaction is carried out in the liquid phase, adequate pressures must exist to maintain this state. Typically, pressures of about atmospheric to 3000 psia are employed, and most preferably, about 200 to 1500 psia, but it is to be emphasized that a precise range of pressures is not a critical parameter of the process, other than it is desired, if possible, to maintain a substantially liquid phase operation. For vapor phase operation, typical pressures are in the range of about 150 to 300 psia.

When the process is carried out in a batch system, the phenol, ammonia and catalyst are first charged to an appropriate vessel capable of withstanding the applied pressure, such as an autoclave, and the mixture is then stirred and heated at the process operating temperature for a desired length of time. The amount of catalyst present is preferably in the range of about 0.1 to 20 wt. % of the charge, and most preferably 3 to 10 wt. %. Ordinarily reaction times of 1 to 20 hours are suitable; greater amounts of DPA generally are produced with longer reaction times. Increased catalyst concentrations also produce greater quantities of products per unit time. When the reaction is carried out in a fixed bed reactor, which is the preferred embodiment for the process, the mixture of phenol, ammonia and aniline is continuously fed and recycled through a bed of the solid heterogeneous acidic alumina catalyst contained in a suitable reaction column or tube. Ordinarily, the stream is passed upwardly through the bed, and the rate of passing the phenol-aniline-ammonia stream through the bed can vary over a wide range. This rate is preferably selected to maintain a liquid hourly space velocity of between 0.01 to 0.50 hr$^{-1}$. The space velocity in this process is determined by dividing the volume of the total phenol plus aniline (total organics) feed per unit time by the volume of catalyst in the bed, i.e., a feed rate of phenol and aniline in liters per hour and the catalyst volume in liters. In the case of liquid phase batch operation, the reaction product mixture is first filtered to remove the solid catalyst and is then treated to separate the evolved water and to recover the DPA and/or aniline products from the phenol, ammonia and aniline mixture. When a fixed bed catalyst system is used there is, of course, no filtration step for the removal of catalyst, and the effluent is ripe for treatment to be separated into the desired product components. It is critical to the process that the unreacted aniline not be taken off as product, instead, together with any unreacted phenol and ammonia, it is recycled back to the reactor for further contacting with fresh makeup feed and the catalyst bed. The recycling of the entire reaction zone effluent, excepting for the DPA product together with whatever amount of aniline product is desired, can lead to a system in which extremely large quantities of aniline are present in the process cycle; e.g., up to ratios of about 10:1 aniline to phenol. The amount of aniline desired as a product, along with the DPA product, can be separated from the reaction mixture and the remainder recycled.

The alumina gel catalysts such as those described in U.S. Pat. Nos. 3,860,650 and 3,944,613 can be used in carrying out the process of this invention, and, in fact, a large number of solid, heterogeneous, acidic alumina catalysts, as well as other similar catalysts, are believed to be useful in the disclosed process. In particular, it is believed that an acid treated alumina gel catalyst containing no more than about 0.2 wt. % alkali metal, that is, an alumina prepared from a precipitated gel form, such as, for example, those currently sold under the ALCOA, Inc., trade name, "H151", are the most preferred catalyst for use in the aforementioned process.

Solvents can be employed if desired, although it is believed that no significant improvements in performance are obtained by their use. Accordingly, any organic solvent that is non-reactive in the reaction media can be used.

As mentioned above, it is a factor of the process of this invention that high selectivities can be obtained and that attractive conversions can be realized. Using the process of this invention, selectivities of the order of 93 to 97% can be achieved along with significant conversions of the reactants. As mentioned, catalyst concentrations and reaction or contact time can influence the conversion rates, and thus the conversion can be varied by changing these two parameters to the extent desired.

The following examples are provided to illustrate the invention in accordance with the principles of this invention but are not construed as limiting the invention in any way except as indicated by the appended claims.

EXAMPLE 1

This example illustrates that when a large excess, e.g., a high recycle of aniline to phenol is present in the system, phenol and ammonia are totally converted to DPA with no net aniline production. An excess of ammonia was used.

A 1" dia. × 14 BWG tube was packed with 1210 cc of ¼" low alkali ALCOA H151 alumina gel catalyst. The reactor was operated at conditions of 220 psig and 370° C.

Four grams per hour of phenol and 36 g/hr of aniline were charged into the reactor, corresponding to an aniline to phenol ratio of 9:1 molar. Ammonia was fed in at a rate of 23 g/hr, creating an ammonia to organic ratio of 3 molar. Phenol conversion was found to be about 95-98%, with a selectivity to DPA of 93%, the remainder being a variety of byproducts. No aniline was seen to have formed. Thus, the 4 g/hr of phenol was converted by the process to about 3.5 g/hr of DPA, with no net aniline make nor conversion. The 36 g/hr of aniline can be recycled to join with a fresh feed stream as can the unconverted ammonia.

EXAMPLE 2

This example illustrates how a net product mix of 30 wt. % DPA/70 wt. % aniline can be produced by reducing the excess recycle of aniline as compared to Example 1. An excess of ammonia is maintained.

Using the same process apparatus as Example 1, 12 g/hr of phenol and 28 g/hr of aniline are fed into the reactor, corresponding to an aniline to phenol molar ratio of 2.3 to 1. Ammonia is fed at a rate of 23 g/hr, creating an ammonia to total organics ratio of 3:1 molar. The reactor effluent consists of approximately 36 g/hr of aniline and 3.6 g/hr of DPA. The 3.6 g/hr of DPA together with 8 g/hr of aniline are separated as reaction product, forming a ratio of 30 wt. % DPA/70 wt. % aniline, and the remaining 28 g/hr of aniline is recycled back to join with additional feed, as is the excess ammonia.

EXAMPLE 3

This example illustrates how a net product mix of 100 wt. % DPA/0 wt. % aniline is produced from just a phenol and ammonia feedstock by providing just enough ammonia feed to satisfy the stoichiometry of the aniline reaction and recycling phenol and aniline.

One mole of ammonia and two moles of phenol fresh feed are combined with 5.7 moles of phenol and 5.7 moles of aniline recycle. Using the same type of catalyst as in Example 1 and in a reaction zone kept at 370° C., and 700 psig and having a liquid space velocity of 0.08 $hr^{-1}$, the one mole of ammonia reacts rapidly with one mole of phenol to form a mole of aniline. Reaction conditions are such that one mole of DPA also forms from the reaction of phenol and aniline. Thus, the net reaction converts two moles of phenol fresh feed into one mole of DPA, with no aniline product formed. Because the ammonia is totally consumed in the early stages of the reaction, it is possible to operate the major portion of the reaction in the liquid phase. The excess, unconverted phenol and aniline is preferably recycled.

EXAMPLE 4

The example is in contrast to Example 3, showing how a product mixture of 47 wt. % DPA/53 wt. % aniline is produced from just a phenol and ammonia feedstock by providing for a stoichiometric amount of ammonia while recycling excess phenol and aniline.

Three moles of ammonia and four moles of phenol fresh feed are fed to the reactor of Example 1, along with the 5.7 moles of phenol and 3.7 moles of aniline. Using the same type of catalyst as Example 1 and keeping the reactor at 370° C., 700 psig with a liquid space velocity of 0.08 $hr^{-1}$, the three moles of ammonia react rapidly with three moles of phenol and form, in situ, three moles of aniline. Reaction conditions are such so that one mole of DPA also forms from the reaction of one mole of phenol and one mole of aniline. Thus the net reaction features reacting four moles of fresh phenol feed to yield one mole of DPA and two moles of aniline, for a product weight ratio of about 47 wt. % DPA/53 wt. % aniline. Because the ammonia is totally consumed in the early stages of the reactor, it is possible to operate the major portion of the reactor in the liquid phase. The excess unconverted aniline and phenol are recycled.

EXAMPLE 5

This example illustrates how high aniline to DPA ratios are obtained by supplying an excess amount of ammonia and not withdrawing aniline.

A 1" dia.×14 BWG tube was packed with 1210 cc of ¼", low alkali, alumina ALCOA H151 catalyst. Phenol was then fed in at a rate of 40 g/hr and ammonia at a rate of 23 g/hr through the tube, creating a molar ratio of about 3 moles of ammonia per mole of phenol. The reactor temperature was 370° C. and the pressure was maintained at 225 psia. No recycling was used, e.g., the recycle ratio is zero. Phenol conversion was found to be in excess of 99% and selectivity was about 90 wt. % to aniline to 10 wt. % DPA. The excess ammonia can be recycled, if desired.

We claim:

1. A process for the formation of diphenylamine and aniline in amounts ranging from about 100:0 to 1:99 wt % DPA:aniline comprising:

contacting a feedstock consisting essentially of phenol and ammonia in a reaction zone with a solid, heterogeneous acidic alumina catalyst and reacting to form aniline in situ, so as to form a mixture in amounts ranging from about 20:1 to 1:100 molar % of phenol plus aniline:ammonia;

reacting the formed in situ aniline in the presence of the solid heterogeneous acidic alumina catalyst with either phenol or a second aniline in the phenol-ammonia-aniline mixture present in the reaction zone to form diphenylamine;

separating the formed diphenylamine and a predetermined amount of aniline as reaction products from the reaction zone mixture;

recycling the remaining phenol-ammonia-aniline stream back to the reaction zone;

continuing the above cycle.

2. A process as claimed in claim 1 wherein the process is carried out in a substantially liquid phase environment.

3. A process as claimed in claim 1 wherein the process is carried out in a substantially vapor phase environment.

4. A process as claimed in claim 1 wherein the reaction zone temperature ranges between about 300° to 420° C.

5. A process as claimed in claim 1 wherein the reaction zone pressure ranges between about 200 to 1500 psia.

6. A process as claimed in claim 1 wherein the process is a continuous process.

7. A process as claimed in claim 1 wherein the process is a batch process.

8. A process as claimed in claim 7 wherein the amount of catalyst present is from about 3 to 10 wt. % of the charge.

9. A process as claimed in claim 1 wherein no substantial amount of aniline is present in the phenol-ammonia feedstock.

10. A process as claimed in claim 1 wherein the liquid hourly space velocity of the organic stream ranges from about 0.02 to 0.50 hr$^{-1}$.

* * * * *